United States Patent
Koslow (10) Patent No.: US 6,872,311 B2
(45) Date of Patent: Mar. 29, 2005

(54) NANOFIBER FILTER MEDIA

(75) Inventor: Evan E. Koslow, Weston, CT (US)

(73) Assignee: Koslow Technologies Corporation, Orange, CT (US)

(*) Notice: Subject to any disclaimer, the term of this patent is extended or adjusted under 35 U.S.C. 154(b) by 164 days.

(21) Appl. No.: 10/341,186

(22) Filed: Jan. 13, 2003

(65) Prior Publication Data

US 2003/0177909 A1 Sep. 25, 2003

Related U.S. Application Data

(60) Provisional application No. 60/354,062, filed on Jan. 31, 2002.

(51) Int. Cl.[7] .......................... B01D 39/00; B01D 24/00
(52) U.S. Cl. ................... 210/502.1; 210/505; 210/506; 210/507; 210/500.1; 55/527; 55/528; 264/203; 428/181
(58) Field of Search ................... 210/505–509, 210/500.1, 502.1; 55/527, 528; 264/203; 428/181

(56) References Cited

U.S. PATENT DOCUMENTS

| | | |
|---|---|---|
| 2,810,646 A | 10/1957 | Wooding et al. |
| 3,047,455 A | 7/1962 | Holmes et al. |
| 3,391,057 A | 7/1968 | Spence et al. |

(List continued on next page.)

OTHER PUBLICATIONS

*The Basic Of HEPA filtration: History of the HEPA filter*; http://www.c-vac.com/history.html; printed Nov. 21, 2001.
*The Basic Of HEPA Filtration: Principles of Filtration*; http://www.c-vac.com/principles.html; printed Nov. 21, 2001.
*The Basic Of HEPA Filtration: HEPA Construction*; http://www.c-vac.com/construction.html; printed Nov. 21, 2001.
*The Basic Of HEPA Filtration: DOP Testing* http://www.c-vac.com/testing.html; printed Nov. 21, 2001.
*Particle Sizes*, http://www.c-vac.com/particlesizes.html; printer Nov. 21, 2001.
Fabbro et al., *Air Flows and Pressure Drop Modelling for Different Ploated Industrial Filters*, Filtration & Separation; Jan./Feb. 2002; pp. 35–40.
Gadney, *Watch Out for Tensile–Testing Pitfalls*; Industrial Heating, Apr. 2002; pp. 34–36.

*Primary Examiner*—Ana Fortuna
(74) *Attorney, Agent, or Firm*—Shirley S. Ma (57) ABSTRACT

The present invention is directed to an air filter medium comprising nanofibers, the filter medium having a thickness of less than 0.25 millimeters, a Figure of Merit of greater than about 0.075, and an efficiency of greater than about 99.9% when capturing aerosol particles of about 0.18 microns in size and a pressure drop of less than about 40 millimeters water column at a flow rate of about 32 liters/minute through a sample 100 cm$^2$ in size. A coating of the nanofibers may also be used to enhance performance of existing filter media by increasing the FOM of the existing filter media. Preferably, the nanofibers are fibrillated.

20 Claims, 1 Drawing Sheet

U.S. PATENT DOCUMENTS

| | | | |
|---|---|---|---|
| 4,293,378 A | 10/1981 | Klein | |
| 4,318,774 A | 3/1982 | Powell et al. | |
| 4,344,775 A | 8/1982 | Klein | |
| 4,376,675 A | 3/1983 | Perrotta | |
| 4,397,907 A | 8/1983 | Rosser et al. | |
| 4,411,948 A | 10/1983 | Ogino et al. | |
| 4,459,332 A | 7/1984 | Giglia | |
| 4,495,030 A | 1/1985 | Giglia | |
| 4,519,873 A | 5/1985 | Amano et al. | |
| 4,565,727 A | 1/1986 | Giglia et al. | |
| 4,929,502 A | 5/1990 | Giglia | |
| 5,015,274 A | 5/1991 | Perry | |
| 5,306,321 A | 4/1994 | Osendorf | |
| 5,395,411 A | 3/1995 | Kobayashi | |
| 5,401,588 A * | 3/1995 | Garvey et al. | 428/703 |
| 5,427,597 A | 6/1995 | Osendorf | |
| 5,593,479 A | 1/1997 | Frey et al. | |
| 5,672,399 A | 9/1997 | Kahlbaugh et al. | |
| 5,761,908 A | 6/1998 | Oas et al. | |
| 6,036,738 A | 3/2000 | Shanbrom | |
| 6,042,769 A * | 3/2000 | Gannon et al. | 264/203 |
| 6,156,086 A * | 12/2000 | Zhang | 55/382 |
| 6,165,572 A | 12/2000 | Kahlbaugh et al. | |
| 6,171,684 B1 | 1/2001 | Kahlbaugh et al. | |
| 6,197,096 B1 | 3/2001 | Cartellone | |
| 6,267,898 B1 * | 7/2001 | Fukuda et al. | 210/767 |
| 6,315,805 B1 * | 11/2001 | Strauss | 55/486 |
| 6,372,004 B1 | 4/2002 | Schultink et al. | |
| 6,419,839 B1 * | 7/2002 | Cox et al. | 210/764 |
| 6,521,321 B2 * | 2/2003 | Kahlbaugh et al. | 428/181 |
| 6,660,172 B2 * | 12/2003 | Koslow | 210/777 |

* cited by examiner

FIG. 1

NANOFIBER FILTER MEDIA

This application claims priority from U.S. Provisional Application Ser. No. 60/354,062 filed on 31 Jan. 2002.

SUMMARY OF THE INVENTION

The present invention is directed to a filter medium comprising: fibrillated fibers having a Canadian Standard Freeness of less than about 45, the filter medium having performance criteria of: a thickness of less than or equal to about 0.25 millimeters and a Figure of Merit of greater than about 0.075, and an efficiency of greater than about 99.9% when capturing aerosol particles of about 0.18 microns in size and a pressure drop of less than about 40 millimeters water column at a flow rate of about 32 liters/minute through a sample 100 cm² in size; and wherein if the filter medium is thinner than 0.25 millimeters, then the efficiency and pressure drop of the thinner filter medium when adjusted to account for a difference in thickness up to 0.25 millimeters thick, can provide a filter medium that meets or exceeds the performance criteria.

In another aspect, the present invention is directed to a filter medium comprising: a mixture of microglass fibers and fibrillated lyocell fibers having a Canadian Standard Freeness of less than about 45, the filter medium having performance criteria of: a thickness of less than or equal to about 0.25 millimeters and a Figure of Merit of greater than about 0.075, and an efficiency of greater than about 99.9% when capturing aerosol particles of about 0.18 microns in size and a pressure drop of less than about 40 millimeters water column at a flow rate of about 32 liters/minute through a sample 100cm² in size; and wherein if the filter medium is thinner than 0.25 millimeters, then the efficiency and pressure drop of the thinner filter medium when adjusted to account for a difference in thickness up to 0.25 millimeters thick, can provide a filter medium that meets or exceeds the performance criteria.

In yet another aspect, the present invention is directed to a filter medium comprising: fibrillated lyocell fibers having a Canadian Standard Freeness of less than about 10, the filter medium having performance criteria of: a thickness of less than or equal to about 0.25 millimeters and a Figure of Merit of greater than about 0.075, and an efficiency of greater than about 99.9% when capturing aerosol particles of about 0.18 microns in size and a pressure drop of less than about 40 millimeters water column at a flow rate of about 32 liters/minute through a sample 100 cm² in size; and wherein if the filter medium is thinner than 0.25 millimeters, then the efficiency and pressure drop of the thinner filter medium when adjusted to account for a difference in thickness up to 0.25 millimeters thick, can provide a filter medium that meets or exceeds the performance criteria.

The present invention includes filter systems incorporating the filter media generally described above.

In still yet another aspect, the present invention is directed to a process of making an air filter medium comprising the steps of: dispersing fibrillated fibers; and forming a layer of the fibrillated fibers having a thickness of less than about 0.25 millimeters such that the filter medium has performance criteria of: a Figure of Merit of greater than about 0.075, and an efficiency of greater than about 99.9% when capturing aerosol particles of about 0.18 microns in size and a pressure drop of less than about 40 millimeters water column at a flow rate of about 32 liters/minute through a sample 100 cm² in size; and wherein if the filter medium is thinner than 0.25 millimeters, then the efficiency and pressure drop of the thinner filter medium when adjusted to account for a difference in thickness up to 0.25 millimeters thick, can provide a filter medium that meets or exceeds the performance criteria.

In still yet another aspect, the present invention is directed to a method of enhancing performance of an existing filter medium comprising the steps of: providing a plurality of nanofibers; wet laying the nanofibers on the existing filter medium wherein the nanofibers are loaded onto the existing filter medium at a rate of about 0.5 g/m² to about 11.0 g/m²; and increasing a Figure of Merit of the existing filter medium by at least about 100%. Preferably, in the step of providing a plurality of fibrillated nanofibers, the nanofibers include microglass fibers, lyocell nanofibers, acrylic nanofibers, or combinations thereof. The method may further include the steps of providing a solid binder wherein the fibrillated nanofibers and solid binder are wet laid on the existing filter medium, and activating the solid binder.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the description of the preferred embodiment(s) which follows taken in conjunction with the accompanying drawings in which:

DETAILED DESCRIPTION OF THE PREFERRED EMBODIMENT(S)

Definitions

"Binder" shall mean a material used principally to hold other materials together.

"Canadian Standard Freeness" or "CSF" shall mean a value for the freeness or drainage rate of pulp as measured by the rate that a suspension of pulp may be drained. This methodology is well known to one having skill in the paper making arts.

"DOP" shall mean dioctyl phanthalate. A monodispersion of DOP droplets having a particle size of 0.18 microns was used for testing the filtration medium of the present invention.

"Fiber" shall mean a solid that is characterized by a high aspect ratio of length to diameter of, for example, several hundred to one. Any discussion of fibers includes whiskers.

"Filter medium" shall mean a material that performs fluid filtration.

"FOM" or "Figure of Merit" shall mean $$[-\log(1-FE)]/\Delta P$$

where FE is the fractional interception efficiency of the filter medium at a specific flow velocity and for a specific particle size. $\Delta P$ is the differential pressure, also referred to as pressure drop or resistance, across the filter medium at a specific flow velocity. In this specification, the standard aerosol is 0.18 microns DOP carried at a flow rate of 32 liters/minute through a filter area of 100 cm². It shall be understood that the FOM value of an anisotropic medium is a constant such that the pressure drop varies in direct proportion to the thickness of the filter medium and log (1−FE) also varies in direct proportion to the thickness of the medium such that the FOM is a constant for a given filter medium regardless of the thickness of the final filter medium.

"Fluid" shall mean a liquid, gas, or combination thereof.

"Forming" shall mean converting a loose, unstructured substance into a cohesive, uniform structure. For example, the conversion of loose fibers into a paper.

"HEPA" filter or filter medium is taken to mean high efficiency particulate air filter or filter medium capable of removing at least 99.97% of all airborne particulate matter 0.3 micron in diameter and larger.

"Intercept" or "interception" are taken to mean interfering with, or stopping the passage of, so as to affect, remove, inactivate or influence.

"Nanofiber" shall mean a fiber having a diameter less than about 3.0 millimeters.

"Nonwoven" means a web or fabric or other medium having a structure of individual fibers that are interlaid, but not in a highly organized manner as in a knitted or woven fabric. Nonwoven webs generally may be prepared by methods that are well known in the art. Examples of such processes include, but are not limited to, and by way of illustration only, meltblowing, spunbonding, carding, and air laying.

"Paper" or "paper-like" shall mean a generally flat, fibrous layer or mat of material formed by a wet laid process.

"Particle" shall mean a solid having a size range from the colloidal to macroscopic, and with no specific limitation on shape, but generally of a limited length to width ratio.

"Sheet" shall mean a roughly two-dimensional structure having a length and a width that are significantly greater than its thickness.

"Whisker" shall mean a filament having a limited aspect ratio and intermediate between the aspect ratio of a particle and a fiber. Any discussion of fibers includes whiskers.

Characteristics of the Filter Medium

The high efficiency particulate air (HEPA) filter medium of the present invention comprises a plurality of nanofibers and a binder formed into a layer having a thickness of less than about 0.25 millimeters and an efficiency of greater than about 99.9% for aerosol particles of about 0.18 microns in diameter when air passes through a 100 cm$^2$ diameter disk of filter medium at a flow rate of about 32 liters/minute at about 20° C. and atmospheric pressure and at a pressure drop of less than about 45 millimeters water column. The filter medium of the present invention makes it possible to increase the amount of filter medium incorporated into a final filter design because it is thin and pleatable, thereby enhancing filter performance. Existing filter systems can be retrofitted with substantially more of the filter medium of the present invention since each layer is much thinner than traditional HEPA materials that have a thickness of 0.38 to 0.457 millimeters, with similar or improved aerosol interception at a modest pressure drop.

Air filters including the filter medium of the present invention are useful in applications such as, for example, air circulation systems in buildings, vehicles, in particular enclosed vehicles, vacuum cleaners, respirator filters, or other applications that require filtered air.

A coating of nanofibers on an existing filter medium can also be used to enhance the performance of an existing filter medium and can provide an increase of more than about 100% in the Figure of Merit (FOM) of an existing filter.

The filter medium can also be electrostatically charged to provide enhanced filtration performance. Further treatment of the filter medium can provide biocidal properties for microbiological interception useful in respirators for nuclear, biological, and chemical (NBC) defense.

There are two fundamental methods for the production of improved air filter media. The first is to produce a material with an enhanced "Figure of Merit" (FOM), roughly equal to the log of particle interception divided by the differential pressure across the filter medium. Although there are variations on the FOM concept, the basic equation is:

$$FOM = [-\log(1-FE)]/\Delta P$$

where FE is the fractional interception efficiency of the filter medium at a specific flow velocity and for a specific particle size, and ΔP is the pressure drop also measured at a specific flow velocity.

When a filter medium is isotropic with depth and operates in the laminar flow regime, then the FOM is basically a constant for such a filter medium regardless of any variations in basis weight for different samples of the filter medium. This is a very useful tool when comparing a variety of filter media. For example, the FOM is usually greatly improved through the application of an electrostatic charge on the air filter medium, or for materials using extremely small fibers that operate in the "slip" regime.

Figure 1:
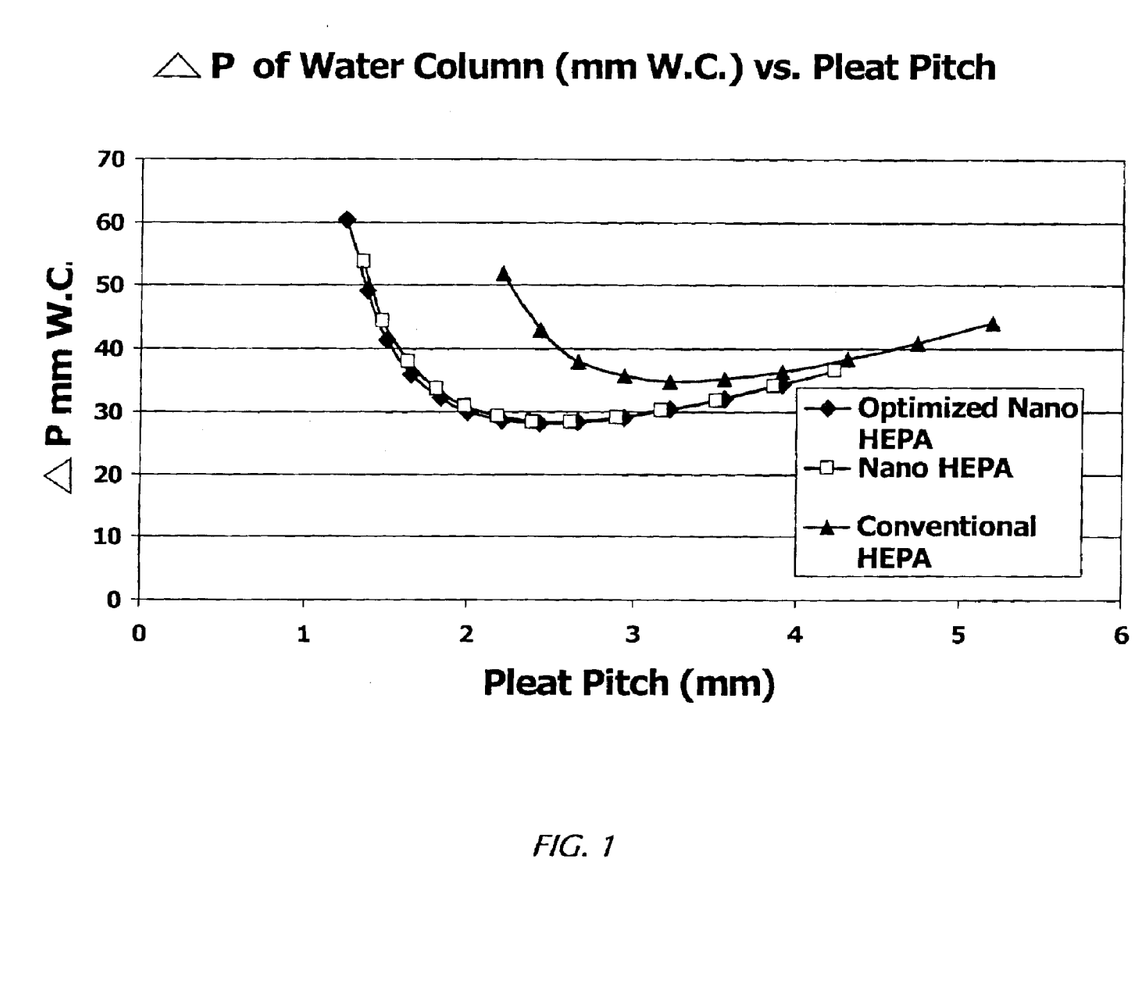
FIG. 1 is a graph illustrating particle interception as the air velocity through the filter medium varies.

However, when two filter media have the same FOM, but one is many times thicker than the other, clearly one would use the thin filter medium because space is almost always at a premium in the design of a filter product. When the filter medium is pleated, the thickness of the filter medium plays a pivotal role in achieving maximum filter surface area. If twice as much filter paper can be packed into a filter, the velocity of air through the filter paper is reduced in half compared to the base case. In addition, the efficiency of particle interception by an air filter improves as the velocity of air through the filter paper declines. This is especially important for small particles that must diffuse to the filter surface. FIG. 1 illustrates particle interception as the air velocity through the filter medium varies. The Optimized Nano HEPA is the HEPA material of the present invention after having been adjusted for thickness. Any reduction in air flow, by adding more filter medium into the filter design (more pleats), made possible through the use of a thin material, provides significant benefits. Additional pleats allow the filter system to have a lower pressure drop and improved particle interception efficiency because it operates at a lower air flow velocity when pleated. Thickness of the filter medium, therefore, indirectly influences both the filtration efficiency and pressure drop in a pleated filter, as it alters the optimum packing of the pleats.

The present invention provides an efficient flat-sheet filter medium with a good FOM value that is also extremely thin. It is possible to produce filter media with the same FOM as current-generation epoxy-glass filter papers, but at only a fraction of the thickness of the glass medium and with similar overall stiffness and tensile properties. The present invention provides the preferred approach to building a pleated air filter.

The Nanofibers

The filter medium of the present invention is comprised of nanofibers that may be organic or inorganic materials including, but not limited to, polymers, engineered resins, ceramics, cellulose, rayon, glass, metal, activated alumina, carbon or activated carbon, silica, zeolites, or combinations thereof. Combinations of organic and inorganic fibers and/or whiskers are contemplated and within the scope of the invention as for example, glass, ceramic, or metal fibers and polymeric fibers may be used together.

When the filter medium is produced by a wet laid process from nanofibers of cellulose or polymer fibers, such fibers should also have a Canadian Standard Freeness of less than or equal to about 45, and can be less than or equal to about 2. Preferably, a significant portion of the fibers should have a diameter less than or equal to about 1000 nanometers, more preferably less than or equal to about 400 nanometers, and fibers less than or equal to about 200 nanometers in diameter are most preferred. It is preferable to chop the fibers to a length of about 1 millimeter to about 8 millimeters, preferably about 2 millimeters to about 6 millimeters, and more preferably about 3 millimeters to about 4 millimeters. Fibrillated fibers are most preferred due to their exceptionally fine dimensions and potentially low cost.

Preferably, fibrillated synthetic cellulose or acrylic fibers, processed in accordance with the present invention, can produce an ultra-fine filter medium of the present invention. Such fibrillated cellulose fibers can be made by direct dissolution and spinning of wood pulp in an organic solvent, such as an amine oxide, and are known as lyocell fibers. Lyocell fibers have the advantage of being produced in a consistent, uniform manner, thus yielding reproducible results, which may not be the case for, for example, natural cellulose fibers. Further, the fibrils of lyocell are often curled. The curls provide a significant amount of fiber entanglement, resulting in a finished filter medium with high dry strength and significant residual wet strength. Furthermore, the fibrillated lyocell fibers may be produced in large quantities using equipment of modest capital cost. It will be understood that fibers other than cellulose may be fibrillated to produce extremely fine fibrils, such as for example, artificial fibers, in particular, acrylic or nylon fibers, or other cellulosic materials.

Combinations of fibrillated and non-fibrillated fibers may be used in the present invention. For example, microglass fibers can be admixed with fibrillated polymeric fibers to decrease the cost of the total fiber mixture and aid dispersion while maintaining the desired performance. Preferably, the microglass fibers have a diameter of about 0.25 micron to about 1 micron, and preferably about 0.5 micron to about 0.75 microns, and more preferably about 0.65 microns. The amount of microglass fibers may be up to about 90% by weight of the filter medium.

A most preferred embodiment comprises nanofibers of fibrillated lyocell having an average diameter of less than about 200 nanometers and a chopped fiber length of about 3 to about 5 millimeters. The fibrillated lyocell fibers can be admixed with a portion of inexpensive microglass fibers to lower costs yet maintain a desired level of efficiency at an acceptable pressure drop.

Enhancing Mechanical Strength of the Filter Medium

The mechanical strength of the filter medium can be enhanced by forming the filter medium on a support layer that does not significantly impede the flow of air passing through the filter medium. The support layer can be any air permeable substrate provided that the pore size of the support layer is not so large that the nanofibers would be pulled through the air permeable substrate under vacuum pressure. The support layer can be a material made from woven, nonwoven, spunbond, meltblown, cellulosic, and other fibrous materials. An example of such a substrate is a spun-bonded polyester, such as REEMAY™ 2004 or REEMAY™ 2275, available from BBA Nonwovens Reemay, Inc., of Old Hickory, Tenn. The support layer can also be treated or made of materials that are resistant to mold, mildew, fungus or bacteria.

Another means of imparting mechanical strength to the filter medium is by admixing a portion of binder with the nanofibers. It is well known in the art that the addition of epoxy, acrylic or other resins to the paper making process can provide enhanced wet strength, but these water-dispersed resins often cause lower permeability in the final product, especially as fiber size decreases. Although these resins and resin systems can be used in the current invention, it is preferable to use thermoplastic or thermoset materials known in the art, and in either powder, particulate or fiber form. The binder is chosen such that the melting point of the binder material is sufficiently lower than the melting point of the nanofibers so that the filter medium can be heated to activate the binder, while the filter medium does not melt and thereby lose porosity. The binder is preferably sufficiently evenly distributed throughout the filter medium such that later, upon activation, the binder will entrap or bond to substantially all the nanofibers.

Useful binder materials include, but are not limited to, polyolefins, polyvinyl halides, polyvinyl esters, polyvinyl ethers, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenol-formaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like. Other potentially applicable materials include polymers such as polystyrenes and acrylonitrile-styrene copolymers, styrene-butadiene copolymers, and other non-crystalline or amorphous polymers and structures.

A more detailed list of binder materials that may be useful in the present invention include polyalkylenes, polyethers, polyvinyl esters, polyvinyl ethers, ethylene-vinyl acetate copolymers, end-capped polyacetals such as poly (oxymethylene) or polyformaldehyde, poly (trichloroacetaidehyde), poly(n-valeraldehyde), poly (acetaldehyde), poly(propionaldehyde), and the like; acrylic polymers, such as polyacrylamide, poly(acrylic acid), poly (methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly (chlorotrifluoroethylene), ethylene-chlorotrifluoroethylene copolymers, poly(vinylidene fluoride), poly(vinyl fluoride), and the like; polyamides, such as poly(6-aminocaproic acid) or poly($\epsilon$-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly-(sulfonyl-1,4-phenyleneoxy-1,4-phenylenesulfonyl-4,4'-biphenylene), and the like; polycarbonates, such as poly (bisphenol A) or poly(carbonyldioxy-1,4-phenyleneisopropylidene-1,4-phenylene), and the like; polyesters, such as poly(ethylene terephthalate), poly (tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly (thio-1,4-phenylene), and the like; polyimides, such as poly (pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), and the like; vinyl polymers, such as poly(vinyl acetate), poly(vinylidene chloride), poly(vinyl chloride), and the like; diene polymers, such as 1,2-poly-1,3-butadiene, 1,4-poly-1,3-butadiene, polyisoprene, polychloroprene, and the like; polystyrenes; copolymers of the foregoing, such as acrylonitrile-butadiene-styrene (ABS) copolymers, and the like, and mixtures thereof.

A range of binder fibers, including polyethylene, polypropylene, acrylic, or polyester-polypropylene or polypropylene-polyethylene bi-component fibers, or others can be used. Preferred fiber binder materials may include FYBREL® synthetic fibers and/or SHORT STUFF® EST-8, both of which are polyolefin based. FYBREL® is a polyolefin based synthetic pulp that is a highly fibrillated fiber and is commercially available from Mitsui Chemical Company, Japan. FYBREL® has excellent thermal moldability and provides a smooth surface to the filter medium. SHORT STUFF® EST-8 is commercially available from MiniFibers, Inc., Pittsburgh, Pa., and is a highly fibrillated, high density polyethylene. Low density polyethylene (LDPE) binder particles, such as MICROTHENE® Grade FN510, manufactured by Equistar Chemicals, L.P. of Tuscola, Ill., is also preferred. Polyvinyl acetate (PVA) can also be used as a binder. A preferred PVA is KURALON™ VPB071 commercially available from Kuraray Company, Ltd., Osaka, Japan.

Preferably, the binder is present in an amount of about 1% to about 35% by weight, more preferably about 3% to about 10%, and most preferably about 5% to about 7%.

Additives

One or more additives either in a particulate, fiber, whisker, or powder form may also be mixed with the nanofibers to aid in the interception of other contaminants or remove moisture and/or odors. Useful additives may include, but are not limited to, metallic particles, activated alumina, activated carbon, silica, polymeric powders and fibers, glass beads or fibers, cellulose fibers, ion-exchange resins, engineered resins, ceramics, zeolites, diatomaceous earth, activated bauxite, fuller's earth, calcium sulfate, super absorbent polymers (SAPs), or combinations thereof. The additives can also be chemically treated to impart microbiological resistance or biocidal capabilities depending upon the particular application. Such additives are preferably present in a sufficient amount such that the air flow in the resultant filter medium is not substantially impeded during use. The amount of additives is dependent upon the particular function of the filtration system.

Method of Making the HEPA Filter Medium of the Present Invention

The HEPA filter medium of the present invention may be made in accordance with processes known to one of skill in the art. Dry laid processes include spun bonding, electrospinning, islands-in-sea processes, fibrillated films, melt blowing, and other dry laid processes known to one of skill in the art. An exemplary dry laid process starts with staple fibers, which can be separated by carding into individual fibers and are then laid together to a desired thickness by an aerodynamic process to form an unbonded fiber sheet. The unbonded fibers can then be subjected to hydraulic jets to both fibrillate and hydroentangle the fibers. A similar process can be performed on certain plastic films that when exposed to high pressure jets of water, are converted into webs of fibrillated fibers.

In a preferred wet laid process, a fiber tow is chopped to a specific length, usually in the range of about 1 millimeter to about 8 millimeters, and in particular, in the range of about 3 millimeters to about 4 millimeters. The chopped fibers are fibrillated in a device having characteristics similar to a blender, or on a large scale, in machines commonly referred to as a "hi-low", a "beater" or a "refiner". The fiber is subjected to repetitive stresses, while further chopping and the reduction of fiber length is minimized. As the fibers undergo these stresses, the fibers split as a result of weaknesses between amorphous and crystalline regions and the Canadian Standard Freeness (CSF), which is determined by a method well known in the art, begins to decline. Samples of the resulting pulp can be removed at intervals, and the CSF used as an indirect measure of the extent of fibrillation. While the CSF value is slightly responsive to fiber length, it is strongly responsive to the degree of fiber fibrillation. Thus, the CSF, which is a measure of how easily water may be removed from the pulp, is a suitable means of monitoring the degree of fiber fibrillation. If the surface area is very high, then very little water will be drained from the pulp in a given amount of time and the CSF value will become progressively lower as the fibers fibrillate more extensively. The fibrillated fiber of a given CSF value can be directly used for producing paper or dewatered on a variety of different devices, including a dewatering press or belt, to produce a dewatered pulp. The dewatered pulp can be subsequently used to make a wet-laid paper. Generally, for application in the present invention, a pulp with a CSF of below 45 is used, and preferably, the CSF should be less than or equal to about 2. The fibers can be directly sent to pulp preparation systems to create a furnish suitable for paper making. A finished weight of the filter medium is preferably about 21 to about 65 $g/m^2$, preferably about 32 to about 48 $g/m^2$ based on a total weight of the filter medium. Fibers that fibrillate in this manner include lyocell and select grades of acrylic, nylon, or other synthetic fibers of incomplete crystallinity.

The filter medium can be electrostatically charged according to known methods in the art such as, for example, corona discharge treatments or chemical treatment of the nanofibers before or after forming the wet or dry laid paper. Electrostatic charge can also be created by triboelectric effects within nanofiber mixtures of fibers such as, for example, a mixture of acrylic and nylon fibers. Electrostatic charge can provide enhanced interception of microparticulates via electrokinetic interception.

Exemplary of a wet laid process includes dispersing a pulp of about 2 CSF fibrillated lyocell fibers in water with mixing in a blender to form a furnish with about 1% to about 2% consistency. Other fibers and binders or ingredients can be added to this dispersion. Thereafter, the complete mixture of ingredients can be directly used in the production of wet laid filter medium.

Improving the FOM of Existing Filter Media Using Nanofiber Coatings

In another embodiment of the present invention, a topical coating of nanofibers on a substrate such as an existing filter medium has been shown to enhance the FOM of the existing filter medium by at least about 100%. The nanofibers are loaded onto the existing filter medium at a rate of about 0.5 $g/m^2$ to about 11.0 $g/m^2$, and preferably about 1.08 $g/m^2$ using a wet laid process. The nanofibers strongly adhere to the substrate and can also be used to adhere other fibers or ingredients onto the substrate as well by acting as a primary binder. A traditional binder material in solid form may be used to enhance adhesion to the substrate although not necessary in all applications.

Preferably, acrylic nanofibers or fibrillated lyocell fibers, alone and in combination with microglass fibers, provide substantial improvement in the FOM of the existing filter medium. The nanofibers can be applied during the original production of the filter medium or coated thereon after production at nominal cost given the small amounts of nanofibers needed. Acrylic nanofibers having a Canadian Standard Freeness of less than about 45, preferably less than about 10, and preferably about 2, and a chopped fiber length of about 3 millimeters to about 8 millimeters can be used. Such acrylic fibers are fibrillated according to known methods in the art. Preferred acrylic staple fibers can be obtained from Sterling Fibers, Inc., Pace, Fla., under the trade designation RES-25; Asahi Kasei Corporation, Tokyo, Japan, under the tradename CASHMILON™; and/or Mitsubishi Rayon America, New York, N.Y., as a 3 millimeter length fibrillatable staple fiber.

In an exemplary treatment of existing air filter media with a nanofiber coating, a fiber tow is chopped to about 3 to about 4 millimeters in length as described above and fibrillated. The fibrillated nanofibers, including the microglass fibers if used, are then wet laid on a sheet of the existing filter medium or other supporting substrate.

EXAMPLES

The following examples are provided to illustrate the present invention and should not be construed as limiting the scope of the invention.

Aerosol interception and air-flow resistance measurements were made using a Model TDA-100P available from Air Techniques, International of Owings Mill, Md. A monodispersion of 0.18 micron oil aerosol particles were was used in the studies. The flow rate was 32 slpm. Tensile strength was measured using a mechanical test station available from Tinius Olsen Testing Machine Company, Inc. of Horsham, Pa. The thickness of the HEPA filter medium or the nanofiber coating on a support layer shown below does not take into account the thickness of any supporting substrate.

Hand sheets of the HEPA filter medium of the present invention were prepared in accordance with the following general procedure. Materials were weighed out and blended with 2.0 L deionized water for at least 3 minutes in a stainless steel Waring blender. When microglass fibers were used, they were blended separately for about 3 minutes prior to mixing with the nanofibers and binder, if present. The fiber mixture was poured into a 30.5×30.5 cm² stainless steel FORMAX™ paper making deckle with a sheet of REEMAY™ 2004 nonwoven laid over the 100 mesh base screen as a support layer. The deckle was filled to a total of about 12 L of water containing the various fibers. A 30.5× 30.5 cm² stainless steel agitator plate having 60 holes of 2 cm diameter was used to plunge the fiber mixture up and down from top to bottom about 8 to 10 times. The water was removed from the fiber mixture by pulling a slight vacuum below the deckle to cause the fibers to form on the REEMAY™ nonwoven. Once the bulk of the water is removed, supplemental dewatering is accomplished with a vacuum pump to remove additional excess moisture and to create a relatively smooth, flat, fairly thin paper-like sheet. The resulting sheet is separated from the screen and combined with a blotter sheet on both top and bottom. The combination of sheets is gently rolled with a 2.27 kg marble rolling pin to remove excess water and smooth out the top surface of the sheet. The sheet is then placed between two fresh and dry blotter sheets and placed on a FORMAX® sheet dryer for about 10 to about 15 minutes at about 120° C. The dried filter medium is separated from the blotter sheets and directly heated on the FORMAX® sheet dryer for about 5 minutes on each side to activate any binder present.

In examples where the nanofibers are coated onto a filter medium or other coarse substrate, the deckle is lined with the selected filter medium or substrate rather than the REEMAY™ nonwoven and the nanofibers are wet laid thereon as described previously.

Examples 1 and 2

HEPA Filter Media with Fibrillated Lyocell and Microglass Nanofibers

These examples illustrate the performance of HEPA filter media made with fibrillated lyocell nanofibers having a Canadian Standard Freeness of about 8 in an aqueous dispersion admixed with microglass fibers having a fiber diameter of 0.65 microns available from Johns Manville Company of Denver, Colo., under the trade designation FIBREGLASS™ #106. Composition and characteristics of the filter media are shown in Tables I and II.

TABLE I

| Ex. # | Lyocell (wt. %) | Sheet Weight (g) | Thickness (mm) | % Efficiency | ΔP (mm H₂O) | Tensile Strength (@ 50 in/min) Force (kg/ft) | Extension (mm) |
|---|---|---|---|---|---|---|---|
| 1 | 30 | 2.8 | 0.2159 | 99.963 | 29.8 | 1.110 | 2.340 |
| 2 | 25 | 4.5 | 0.2921 | 100 | 48.9 | 1.150 | 1.930 |

Examples 3 through 7

HEPA Filter Media with Fibrillated Lyocell and Microglass Nanofibers

Examples 3 through 7 were made with fibrillated lyocell nanofibers having a Canadian Standard Freeness of about 2 in an aqueous dispersion admixed with FIBREGLASS™ #106 microglass fibers. KURALON™ polyvinyl acetate (PVA), commercially available from Kuraray Company, Ltd., Osaka, Japan, was used as a binder in these and examples below. Example 3 further included MICROTHENE® Grade FN510 as a binder. The MICROTHENE® contains 0.5% by wt. amorphous precipitated silica. Compositions are shown in Table II. Characteristics of the filter media are shown in Table III.

TABLE II

| Ex. # | Lyocell (wt. %) | Glass (wt. %) | PVA (wt. %) | FN510 (wt. %) |
|---|---|---|---|---|
| 3 | 5 | 85 | 7.5 | 7.5 |
| 4 | 2.5 | 90 | 7.5 | — |
| 5 | 2.5 | 92.5 | 5 | — |

TABLE II-continued

| Ex. # | Lyocell (wt. %) | Glass (wt. %) | PVA (wt. %) | FN510 (wt. %) |
|---|---|---|---|---|
| 6 | 2 | 95 | 3 | — |
| 7 | 2 | 95 | 3 | — |

TABLE III

| | | Sheet | | | | Tensile Strength (@ 50 in/min) | |
|---|---|---|---|---|---|---|---|
| Ex. # | Lyocell (wt. %) | Weight (g/ft$^2$) | Thickness (mm) | % Efficiency | ΔP (mm H$_2$O) | Force (kg/ft) | Extension (mm) |
| 3 | 5 | 4.0 | 0.2413 | 99.969 | 36.7 | 1.170 | 1.025 |
| 4 | 2.5 | 4.5 | 0.2540 | 99.966 | 35.57 | 2.938 | 1.943 |
| 5 | 2.5. | 4.5 | 0.2794 | 99.975 | 32.20 | 1.938 | 1.469 |
| 6 | 2 | 4.5 | 0.2794 | 99.979 | 30.40 | 1.608 | 1.227 |
| 7 | 2 | 4.5 | 0.2540 | 99.9945 | 33.57 | 1.073 | 0.973 |

The HEPA filter media of Examples 1 through 7 show excellent efficiency in capturing 0.18 micron aerosol particles at a thickness significantly less than traditional HEPA materials.

Examples 8 through 23

HEPA Filter Media with CSF 2 Fibrillated Lyocell and Microglass Nanofibers

These examples further show the performance of the HEPA filter media of the present invention made with fibrillated lyocell nanofibers and FIBREGLASS #106 microglass fibers without binder and with varying amounts of different binders as shown in the legend below. The binders used are PVA and MICROTHENE® Grade FN-510 with 0.5% by weight of amorphous precipitated silica based on a total weight of the MICROTHENE® and silica.

TABLE IV

| Ex. # | Lyocell (wt. %) | Glass (wt. %) | PVA (wt. %) | FN510 (wt. %) |
|---|---|---|---|---|
| 8 | 2.5 | 90 | 7.5 | — |
| 9 | 2.5 | 92.5 | 5 | — |
| 10 | 2.5 | 90 | 7.5 | — |
| 11 | 10 | 65 | — | 25 |
| 12 | 10 | 75 | — | 15 |
| 13 | 10 | 80 | — | 10 |
| 14 | 7.5 | 85 | — | 7.5 |
| 15 | 5 | 80 | 7.5 | 7.5 |
| 16 | 2.5 | 90 | 7.5 | — |
| 17 | 2.5 | 92.5 | 5 | — |
| 18 | 2.5 | 95 | 2.5 | — |
| 19 | 2 | 95 | 3 | — |
| 20 | 30 | 70 | — | — |

TABLE V

| | Sheet | | | ΔP | Tensile Strength (@ 50 in/min) | |
|---|---|---|---|---|---|---|
| Ex. # | Weight (g/ft$^2$) | Thickness (mm) | % Efficiency | (mm H$_2$O) | Force (kg/ft) | Extension (mm) |
| 8 | 4.5 | 0.2413 | 99.9988 | 34.30 | 0.143 | 1.210 |
| 9 | 4.5 | 0.2413 | 99.9983 | 35.00 | 0.562 | 1.625 |
| 10 | 4.23 | 0.2413 | 99.9906 | 37.00 | 0.3195 | 0.835 |
| 11 | 5.0 | 0.2667 | 99.9945 | 37.30 | 0.4770 | 1.150 |
| 12 | 5.0 | 0.3302 | 99.9994 | 37.60 | 0.298 | 1.278 |
| 13 | 5.0 | 0.3175 | 99.9996 | 37.00 | 0.398 | 1.645 |
| 14 | 5.0 | 0.3302 | 99.9998 | 38.40 | 0.2795 | 1.442 |
| 15 | 4.0 | 0.2159 | 99.9810 | 27.30 | 0.208 | 1.310 |
| 16 | 4.0 | 0.2540 | 99.9880 | 29.40 | 0.251 | 0.978 |
| 17 | 4.0 | 0.2413 | 99.9929 | 32.80 | 0.211 | 0.733 |
| 18 | 4.0 | 0.2540 | 99.9870 | 32.00 | 0.252 | 0.735 |
| 19 | 4.0 | 0.2540 | 99.9850 | 33.80 | 0.446 | 0.883 |
| 20 | 3.0 | 0.1397 | 99.938 | 27.50 | 0.727 | 1.795 |

All examples show excellent efficiency in capturing 0.18 micron aerosol particles, and therefore, would exceed the performance of traditional HEPA materials.

Examples 21 through 35

HEPA Filter Media with CSF 2 Fibrillated Lyocell and Microglass Nanofibers with Varying Amounts of PVA Binder These examples illustrate the differing performance of the HEPA filter media when made with varying amounts of PVA binder. Compositions of the filter media are shown in Table VI with performance results shown in Table VII.

TABLE VI

| Ex. # | Lyocell (wt. %) | Glass (wt. %) | PVA (wt. %) |
|---|---|---|---|
| 21 | 2.5 | 90 | 7.5 |
| 22 | 2.5 | 90 | 7.5 |
| 23 | 2.5 | 92.5 | 5 |
| 24 | 2.5 | 92.5 | 5 |

TABLE VI-continued

| Ex. # | Lyocell (wt. %) | Glass (wt. %) | PVA (wt. %) |
|---|---|---|---|
| 25 | 2.5 | 95 | 2.5 |
| 26 | 2.5 | 95 | 2.5 |
| 27 | 2 | 95 | 3 |
| 28 | 2 | 95 | 3 |
| 29 | 2.5 | 90 | 7.5 |
| 30 | 2.5 | 92.5 | 5 |
| 31 | 2.5 | 95 | 2.5 |
| 32 | 2 | 95 | 3 |
| 33 | 29 | 70 | 1 |
| 34 | 29 | 70 | 1 |
| 35 | 28.5 | 70 | 1.5 |

TABLE VII

| Sheet Ex. # | Weight (g/ft$^2$) | Thickness (mm) | % Efficiency | ΔP (mm H$_2$O) | Tensile Strength (@ 50 in/min) Force (kg/ft) | Tensile Strength (@ 50 in/min) Extension (mm) |
|---|---|---|---|---|---|---|
| 21 | 4.0 | 0.3302 | 99.9270 | 31.40 | 0.896 | 0.868 |
| 22 | 4.0 | 0.2159 | 99.9958 | 29.60 | 0.176 | 0.980 |
| 23 | 4.0 | 0.3429 | 99.970 | 32.85 | 1.043 | 1.208 |
| 24 | 4.0 | 0.2159 | 99.9976 | 32.00 | 0.234 | 1.195 |
| 25 | 4.0 | 0.2540 | 99.9900 | 32.20 | 0.407 | 0.628 |
| 26 | 4.0 | 0.3175 | 99.9860 | 32.50 | 0.876 | 1.173 |
| 27 | 4.0 | 0.3048 | 99.9903 | 34.90 | 0.322 | 0.705 |
| 28 | 4.0 | 0.2159 | 99.9961 | 34.85 | 0.547 | 1.730 |
| 29 | 4.5 | 0.3683 | 99.9710 | 36.45 | 1.561 | 1.300 |
| 30 | 4.5 | 0.3810 | 99.9870 | 33.25 | 1.402 | 1.453 |
| 31 | 4.5 | 0.3429 | 99.9956 | 36.10 | 0.441 | 0.778 |
| 32 | 4.5 | 0.4064 | 99.9956 | 37.60 | 1.011 | 1.055 |
| 33 | 3.0 | 0.1778 | 99.9805 | 35.63 | 0.8705 | 1.158 |
| 34 | 3.0 | 0.1651 | 99.9880 | 35.23 | 0.629 | 1.083 |
| 35 | 3.0 | 0.1829 | 99.9880 | 35.23 | 0.793 | 1.203 |

The examples in Table VII show excellent interception efficiency of 0.18 micron aerosol particles with modest pressure drop.

Examples 36 through 38

Comparison of Pleated and Unpleated HEPA Filter Media with CSF 2 Fibrillated Lyocell and Microglass Nanofibers with Varying Amounts of PVA Binder These examples illustrate that the HEPA filter media of the present invention when pleated (denoted by the letter P in Table IX) retain its original unpleated performance. Lyocell nanofibers having a Canadian Standard Freeness of 2 were used in making the filter media. PVA was the binder when used.

TABLE VIII

| Ex. # | Lyocell (wt. %) | Glass (wt. %) | PVA (wt. %) |
|---|---|---|---|
| 36 | 29.5 | 70 | 0.5 |
| 37 | 30 | 70 | — |
| 38 | 25 | 70 | 5 |

TABLE IX

| Sheet Ex. # | Weight (g/ft$^2$) | Thickness (mm) | % Efficiency | ΔP (mm H$_2$O) | Tensile Strength (@ 50 in/min) Force (kg/ft) | Tensile Strength (@ 50 in/min) Extension (mm) |
|---|---|---|---|---|---|---|
| 36 | 3.0 | 0.1651 | 99.985 | 34.95 | 0.741 | 1.053 |
| 36P |  |  | 99.985 | 34.90 |  |  |
| 37 | 3.0 | 0.1651 | 99.990 | 36.05 | 0.756 | 1.168 |
| 37P |  |  | 99.988 | 35.3 |  |  |
| 38 | 3.0 | 0.1651 | 99.988 | 33.20 | 0.704 | 1.965 |
| 38P |  |  | 99.988 | 33.40 |  |  |

Examples 39 through 66

HEPA Filter Media with CSF 2 Fibrillated Lyocell and Microglass Nanofibers with Varying Amounts of EST-8 Binder These examples illustrate the differing performance of the HEPA filter media when varying amounts of EST-8 polyethylene fibers are used as the binder.

TABLE X

| Ex. # | Lyocell (wt. %) | EST-8 (wt. %) | Glass (wt. %) | Ex. # | Lyocell (wt. %) | EST-8 (wt. %) | Glass (wt. %) |
|---|---|---|---|---|---|---|---|
| 39 | 10 | 15 | 75 | 53 | 10 | 15 | 75 |
| 40 | 10 | 10 | 80 | 54 | 10 | 10 | 80 |
| 41 | 15 | 15 | 70 | 55 | 15 | 15 | 70 |
| 42 | 5 | 25 | 70 | 56 | 5 | 25 | 70 |
| 43 | 10 | 20 | 70 | 57 | 10 | 20 | 70 |
| 44 | 10 | 25 | 65 | 58 | 10 | 25 | 65 |
| 45 | 15 | 25 | 60 | 59 | 15 | 25 | 60 |
| 46 | 25 | 15 | 60 | 60 | 25 | 15 | 60 |
| 47 | 20 | 20 | 60 | 61 | 20 | 20 | 60 |
| 48 | 20 | 20 | 60 | 62 | 20 | 20 | 60 |
| 49 | 20 | 20 | 60 | 63 | 20 | 20 | 60 |
| 50 | 10 | 30 | 60 | 64 | 10 | 30 | 60 |
| 51 | 30 | 10 | 60 | 65 | 30 | 10 | 60 |
| 52 | 30 | 10 | 60 | 66 | 30 | 10 | 60 |

TABLE XI

| Sheet Ex. # | Weight (g/ft$^2$) | Thickness (mm) | % Efficiency | ΔP (mm H$_2$O) | Tensile Strength (@ 50 in/min) Force (kg/ft) | Tensile Strength (@ 50 in/min) Extension (mm) |
|---|---|---|---|---|---|---|
| 39 | 4.0 | 0.2667 | 99.9934 | 38.40 | 0.713 | 1.905 |
| 40 | 4.0 | 0.2540 | 99.9972 | 38.15 | 0.587 | 1.430 |
| 41 | 3.5 | 0.2286 | 99.9710 | 32.80 | 1.010 | 1.993 |
| 42 | 3.5 | 0.2032 | 99.9640 | 31.20 | 0.461 | 1.265 |
| 43 | 3.5 | 0.1905 | 99.9710 | 33.05 | 0.674 | 1.803 |
| 44 | 3.5 | 0.2032 | 99.9380 | 32.55 | 0.926 | 2.268 |
| 45 | 4.0 | 0.2032 | 99.9600 | 36.60 | 1.073 | 2.000 |
| 46 | 3.0 | 0.1778 | 99.890 | 32.60 | 1.041 | 1.745 |
| 47 | 3.5 | 0.2159 | 99.9630 | 38.25 | 1.136 | 1.740 |
| 48 | 3.0 | 0.1778 | 99.880 | 32.30 | 1.363 | 2.070 |
| 49 | 3.25 | 0.1829 | 99.890 | 32.90 | 1.427 | 2.216 |
| 50 | 3.5 | 0.2032 | 99.880 | 30.50 | 0.642 | 1.598 |
| 51 | 3.25 | 0.1829 | 99.964 | 39.05 | 1.394 | 2.055 |
| 52 | 3.0 | 0.1829 | 99.944 | 36.65 | 1.319 | 2.090 |
| 53 | 4.0 | 0.2667 | 99.9934 | 38.4 | 0.713 | 1.905 |
| 54 | 4.0 | 0.2540 | 99.9972 | 38.15 | 0.587 | 1.430 |
| 55 | 3.5 | 0.2286 | 99.971 | 32.80 | 1.010 | 1.993 |
| 56 | 3.5 | 0.2032 | 99.964 | 31.2 | 0.461 | 1.265 |
| 57 | 3.5 | 0.1905 | 99.971 | 33.05 | 0.674 | 1.803 |
| 58 | 3.5 | 0.2032 | 99.938 | 32.55 | 0.926 | 2.268 |
| 59 | 4.0 | 0.2032 | 99.960 | 36.60 | 1.073 | 2.000 |

TABLE XI-continued

| Ex. # | Sheet Weight (g/ft$^2$) | Thickness (mm) | % Efficiency | ΔP (mm H$_2$O) | Tensile Strength (@ 50 in/min) Force (kg/ft) | Extension (mm) |
|---|---|---|---|---|---|---|
| 60 | 3.0 | 0.1778 | 99.890 | 32.60 | 1.041 | 1.745 |
| 61 | 3.5 | 0.2159 | 99.963 | 38.25 | 1.136 | 1.740 |
| 62 | 3.0 | 0.1778 | 99.880 | 32.3 | 1.363 | 2.070 |
| 63 | 3.25 | 0.1829 | 99.890 | 32.90 | 1.427 | 2.216 |
| 64 | 3.5 | 0.2032 | 99.880 | 30.5 | 0.642 | 1.598 |
| 65 | 3.25 | 0.1829 | 99.964 | 39.05 | 1.394 | 2.055 |
| 66 | 3.0 | 0.1829 | 99.944 | 36.65 | 1.319 | 2.090 |

Examples 67 through 71

Comparison of Pleated and Unpleated HEPA Filter Media with CSF 2 Fibrillated Lyocell and Microglass Nanofibers with Varying Amounts of EST-8 Binder The following examples compare the performance of the pleated and unpleated HEPA filter media made with 30% by weight lyocell nanofibers, 60% by weight glass microfibers (FIBREGLASS #106), and 10% by weight EST-8 as a binder.

TABLE XII

| Ex. # | Sheet Weight (g/ft$^2$) | Thickness (mm) | % Efficiency | ΔP (mm H$_2$O) | Tensile Strength (@ 50 in/min) Force (kg/ft) | Extension (mm) |
|---|---|---|---|---|---|---|
| 67 | 3.25 | 0.1905 | 99.960 | 39.45 | 1.254 | 1.655 |
| 67P | | | 99.963 | 39.00 | | |
| 68 | 3.0 | 0.1651 | 99.959 | 38.45 | 1.348 | 2.375 |
| 68P | | | 99.959 | 38.70 | | |
| 69 | 3.25 | 0.1905 | 99.960 | 39.5 | 1.254 | 1.655 |
| 69P | | | 99.963 | 39.00 | | |
| 70 | 3.25 | 0.1905 | 99.967 | 39.65 | 1.282 | 1.521 |
| 70P | | | 99.971 | 41.00 | | |
| 71 | 3.0 | 0.1651 | 99.959 | 38.45 | 1.348 | 2.375 |
| 71P | | | 99.959 | 38.65 | | |

Again, the pleated filters show essentially the same performance characteristics as the unpleated filter. All would have excellent interception capabilities of submicron particles since the efficiency tested herein was with 0.18 micron aerosol particles. The tensile strength is also optimal for pleating. The benefits obtained in interception efficiency offsets the slightly higher resistance.

Examples 72 through 74

Improvements in FOM of Existing Filter Media with Nanofiber Coatings

The following examples illustrate the increase in FOM, and thereby filter performance, of existing filter media loaded with 0.15 g/ft$^2$ (dry weight) of nanofibers. All measurements were taken with 0.18 micron aerosol particles at a flow rate of 32 slpm on a 100 cm$^2$ jig. The original filter medium is denoted by FM and is defined by its fractional aerosol penetration, air-flow resistance, and FOM. FM1 and FM2 are a nonwovens. In Example 72, original filter medium FM1 was coated with 25% acrylic nanofibers having a Canadian Standard Freeness of about 2, and 75% FIBREGLASS #106 microglass fibers using a wet laid process as described above. The acrylic fibers in Example, 72 were obtained from Mitsubishi Rayon America. In Example 73, the original filter medium is coated with 25% lyocell fibers having a Canadian Standard Freeness of about 2, and 75% FIBREGLASS #106. In Example 74, original filter medium FM1 was coated with 25% fibrillated lyocell nanofibers having a Canadian Standard Freeness of about 2. In Example 75, original filter medium FM2 was coated with 100% acrylic nanofibers also from Mitsubishi Rayon America. As seen in Table VIII, the addition of a small amount of nanofiber to the existing filter media significantly boosts the FOM, thereby enhancing the performance of the filter media.

TABLE XIII

| Ex # | Fractional Penetration | ΔP (mm H$_2$O) | FOM | Improvement in FOM |
|---|---|---|---|---|
| FM1 | 0.953 | 0.5 | 0.0397 | |
| 72 | 0.592 | 2.7 | 0.0843 | 112% |
| 73 | 0.636 | 1.95 | 0.1008 | 154% |
| 74 | 0.472 | 2.25 | 0.1449 | 265% |
| FM2 | 0.950 | 0.1 | 0.2328 | |
| 75 | 0.736 | 0.2 | 0.6656 | 186% |

Examples 76 through 79

Improvements in FOM of Engine Filter Paper with Nanofiber Coatings

The following examples illustrate the increase in FOM, and thereby filter performance, of an existing filter medium loaded with 1.6 g/m$^2$ (dry weight) of nanofibers. The original filter medium, denoted as FM3, is a standard, resin-bonded cellulose filter medium used in standard automotive engine air in-take filters. Penetration was tested with 0.18 micron aerosol particles at a flow rate of 32 splm on a 100 cm$^2$ jig. Example 76 was coated with fibrillated lyocell nanofibers having a Canadian Standard Freeness of about 2. Examples 77 and 78 were coated with about 25% fibrillated lyocell nanofibers and about 75% FIBREGLASS #106 microglass fibers. Example 79 was coated with about 25% acrylic nanofibers having a Canadian Standard Freeness of about 2, and about 75% FIBREGLASS #106 microglass fibers. Example 79 used acrylic nanofibers obtained from Mitsubishi Rayon America and fibrillated in 3 millimeter lengths. As shown in Table IX, significant improvements in FOM are obtained with the addition of small amounts of nanofibers coated thereon. Such small amounts of nanofibers are an economical way of improving filter performance for a low cost filter.

TABLE XIV

| Ex # | Fractional Penetration | ΔP (mm H$_2$O) | FOM | Improvement in FOM |
|---|---|---|---|---|
| FM3 | 0.906 | 4.1 | 0.0105 | |
| 76 | 0.525 | 11.9 | 0.0235 | 124% |
| 77 | 0.420 | 8.25 | 0.0457 | 335% |
| 78 | 0.742 | 7.85 | 0.0476 | 353% |
| 79 | 0.405 | 8.2 | 0.0478 | 355% |

While the present invention has been particularly described, in conjunction with a specific preferred embodiment, it is evident that many alternatives, modifications and variations will be apparent to those skilled in the art in light of the foregoing description. It is, therefore, contemplated that the appended claims will embrace any such alternatives, modifications and variations as falling within the true scope and spirit of the present invention.

What is claimed is:

1. A filter medium comprising:
fibrillated fibers having a Canadian Standard Freeness of less than about 45, said filter medium having performance criteria of:
a thickness of less than or equal to about 0.25 millimeters and a Figure of Merit of greater than about 0.075, and
an efficiency of greater than about 99.9% when capturing aerosol particles of about 0.18 microns in size and a pressure drop of less than about 40 millimeters water column at a flow rate of about 32 liters/minute through a sample 100 cm$^2$ in size; and
wherein if said filter medium is thinner than 0.25 millimeters, then the efficiency and pressure drop of the thinner filter medium is adjusted to account for a difference in thickness up to 0.25 millimeters thick, to provide a filter medium that meets or exceeds the performance criteria.

2. A filter medium of claim 1 wherein said fibrillated fibers have a Canadian Standard Freeness of less than about 10.

3. A filter medium of claim 1 further including a support layer comprising a material selected from the group consisting of wovens, nonwovens, spunbonds, meltblowns, cellulose, and other fibrous materials.

4. A filter medium of claim 1 wherein said fibrillated fibers are wet laid to form said filter medium.

5. An air filter comprising the filter medium of claim 1.

6. A filter medium comprising:
fibrillated fibers having a Canadian Standard Freeness of less than about 45 and microglass fibers, said filter medium having:
a thickness of less than or equal to about 0.25 millimeters and a Figure of Merit of greater than about 0.075, and
an efficiency of greater than about 99.9% when capturing aerosol particles of about 0.18 microns in size, and a pressure drop of less than about 40 millimeters water column at a flow rate of about 32 liters/minute through a sample size 100 cm$^2$; and
wherein if said filter medium is thinner than 0.25 millimeters, then the efficiency and pressure drop of the thinner filter medium is adjusted to account for a difference in thickness up to 0.25 millimeters thick, meets or exceeds the efficiency of greater than about 99.9% when capturing aerosol particles of about 0.18 microns in size, and a pressure drop of less than about 40 millimeters water column at a flow rate of about 32 liters/minute through a sample size 100 cm$^2$.

7. A filter medium comprising:
fibrillated fibers having a Canadian Standard Freeness of less than about 45 wherein said fibrillated fibers are electrostatically charged or produce a triboelectric charge, said filter medium having:
a thickness of less than or equal to about 0.25 millimeters and a Figure of Merit of greater than about 0.075, and
an efficiency of greater than about 99.9% when capturing aerosol particles of about 0.18 microns in size, and a pressure drop of less than about 40 millimeters water column at a flow rate of about 32 liters/minute through a sample size 100 cm$^2$; and
wherein if said filter medium is thinner than 0.25 millimeters, then the efficiency and pressure drop of the thinner filter medium is adjusted to account for a difference in thickness up to 0.25 millimeters thick, to meet or exceeds the efficiency of greater than about 99.9% when capturing aerosol particles of about 0.18 microns in size, and a pressure drop of less than about 40 millimeters water column at a flow rate of about 32 liters/minute through a sample size 100 cm$^2$.

8. A filter medium comprising:
fibrillated fibers having a Canadian Standard Freeness of less than about 45 and an additive selected from the group consisting of activated carbon, activated alumina zeolites, diatomaceous earth, silicates, aluminosilicates, titanates, bone char, calcium hydroxyapatite, manganese oxides, iron oxides, magnesia, perlite, talc, polymeric particulates, clay, iodated resins, ion exchange resins, ceramics, or combinations thereof, said filter medium having:
a thickness of less than or equal to about 0.25 millimeters and a Figure of Merit of greater than about 0.075, and
an efficiency of greater than about 99.9% when capturing aerosol particles of about 0.18 microns in size, and a pressure drop of less than about 40 millimeters water column at a flow rate of about 32 liters/minute through a sample size 100 cm$^2$; and
wherein if said filter medium is thinner than 0.25 millimeters, then the efficiency and pressure drop of the thinner filter medium is adjusted to account for a difference in thickness up to 0.25 millimeters thick, to meet or exceeds the efficiency of greater than about 99.9% when capturing aerosol particles of about 0.18 microns in size, and a pressure drop of less than about 40 millimeters water column at a flow rate of about 32 liters/minute through a sample size 100 cm$^2$.

9. A filter medium of claim 8 wherein said additive is chemically treated to impart microbiological resistance or biocidal capabilities to said filter medium.

10. A filter medium comprising:
fibrillated fibers comprising lyocell, acrylic, nylon or combinations thereof, having a Canadian Standard Freeness of less than about 45 admixed with microglass fibers, said filter medium having performance criteria of:
a thickness of less than or equal to about 0.25 millimeters and a Figure of Merit of greater than about 0.075, and
an efficiency of greater than about 99.9% when capturing aerosol particles of about 0.18 microns in size and a pressure drop of less than about 40 millimeters water column at a flow rate of about 32 liters/minute through a sample 100 cm$^2$ in size; and
wherein if said filter medium is thinner than 0.25 millimeters, then the efficiency and pressure drop of the thinner filter medium is adjusted to account for a difference in thickness up to 0.25 millimeters thick, to provide a filter medium that meets or exceeds the performance criteria.

11. A filter medium comprising
fibrillated fibers comprising lyocell, acrylic, nylon or combinations thereof, having a Canadian Standard Freeness of less than about 45 admixed with microglass fibers, wherein the microglass fibers have a fiber diameter of less than about 1 micron, said filter medium having performance criteria of:
a thickness of less than or equal to about 0.25 millimeters and a Figure of Merit of greater than about 0.075, and
an efficiency of greater than about 99.9% when capturing aerosol particles of: about 0.18 microns in size and a pressure drop of less than about 40 millimeters water column at a flow rate of about 32 liters/minute through a sample 100 cm² in size; and wherein if said filter medium is thinner than 0.25 millimeters, then the efficiency and pressure drop of the thinner filter medium is adjusted to account for a difference in thickness up to 0.25 millimeters thick, can provide a filter medium that meets or exceeds the performance criteria.

12. A filter medium comprising:
wherein the fibrillated fibers comprising lyocell, acrylic, nylon or combinations thereof have a fiber diameter of about 250 nanometers, a Canadian Standard Freeness of less than about 45, and a chopped fiber length of about 1 to about 8 millimeters, admixed with microglass fibers, said filter medium having performance criteria of:
a thickness of less than or equal to about 0.25 millimeters and a Figure of Merit of greater than about 0.075, and
an efficiency of greater than about 99.9% when capturing aerosol particles of about 0.18 microns in size and a pressure drop of less than about 40 millimeters water column at a flow rate of about 32 liters/minute through a sample 100 cm² in size; and
wherein if said filter medium is thinner than 0.25 millimeters, then the efficiency and pressure drop of the thinner filter medium is adjusted to account for a difference in thickness up to 0.25 millimeters thick, can provide a filter medium that meets or exceeds the performance criteria.

13. A filter medium comprising:
fibrillated fibers comprising lyocell, acrylic, nylon or combinations thereof, having a Canadian Standard Freeness of less than about 45 admixed with microglass fibers, wherein the fibrillated fibers comprising lyocell, acrylic, nylon or combinations thereof are present in an amount of about 5% to about 40% by weight of said filter medium, said filter medium having performance criteria of:
a thickness of less than or equal to about 0.25 millimeters and a Figure of Merit of greater than about 0.075, and
an efficiency of greater than about 99.9% when capturing aerosol particles of about 0.18 microns in sire and a pressure drop of less than about 40 millimeters water column at a flow rate of about 32 liters/minute through a sample 100 cm² in size; and
wherein if said filter medium is thinner than 0.25 millimeters, then the efficiency and pressure drop of the thinner filter medium is adjusted to account for a difference in thickness up to 0.25 millimeters thick, to provide a filter medium that meets or exceeds the performance criteria.

14. An air filter comprising a filter medium comprising:
fibrillated fibers comprising lyocell, acrylic, nylon or combinations thereof, having a Canadian Standard Freeness of less than about 45 admixed with microglass fibers, said filter medium having performance criteria of:
a thickness of less than or equal to about 0.25 millimeters and a Figure of Merit of greater than about 0.075, and
an efficiency of greater than about 99.9% when capturing aerosol particles of about 0.18 microns in size and a pressure drop of less than about 40 millimeters water column at a flow rate of about 32 liters/minute through a sample 100 cm² in size; and
wherein if said filter medium is thinner than 0.25 millimeters, then the efficiency and pressure drop of the thinner filter medium is adjusted to account for a difference in thickness up to 0.25 millimeters thick, to provide a filter medium that meets or exceeds the performance criteria.

15. A filter medium comprising:
fibrillated fibers having a Canadian Standard Freeness of less than about 10, said filter medium having performance criteria of:
a thickness of less than or equal to about 0.25 millimeters and a Figure of Merit of greater than about 0.075, and
an efficiency of greater than about 99.9% when capturing aerosol particles of about 0.18 microns in size and a pressure drop of less than about 40 millimeters water column at a flow rate of about 32 liters/minute through a sample 100 cm² in size; and
wherein if said filter medium is thinner than 0.25 millimeters, then the efficiency and pressure drop of the thinner filter medium is adjusted to account for a difference in thickness up to 0.25 millimeters thick, to provide a filter medium that meets or exceeds the performance criteria.

16. A filter medium according to claim 15 wherein said fibrillated fibers comprise lyocell, acrylic, nylon or combinations thereof.

17. A process of making an air filter medium comprising the steps of:
dispersing fibrillated fibers; and
forming a layer of the fibrillated fibers having a thickness of less than about 0.25 millimeters such that said filter medium has performance criteria of:
a Figure of Merit of greater than about 0.075, and
an efficiency of greater than about 99.9% when capturing aerosol particles of about 0.18 microns in size and a pressure drop of less than about 40 millimeters water column at a flow rate of about 32 liters/minute through a sample 100 cm² in size; and wherein if said filter medium is thinner than 0.25 millimeters, then the efficiency and pressure drop of the thinner filter medium is adjusted to account for a difference in thickness up to 0.25 millimeters thick, to provide a filter medium that meets or exceeds the performance criteria.

18. A method of enhancing performance of an existing filter medium comprising the steps of:
providing a plurality of fibrillated nanofibers;
wet laying or coating from a fluid suspension the fibrillated nanofibers onto the existing filter medium wherein the fibrillated nanofibers are loaded onto the existing filter medium at a rate of about 0.5 g/m² to about 11.0 g/m²; and
increasing a Figure of Merit of the existing filter medium by at least about 100%.

19. A method of claim 18 wherein in the step of providing a plurality of fibrillated nanofibers, the nanofibers comprise lyocell nanofibers, acrylic nanofibers, nylon nanofibers or combinations thereof, and further including microglass fibers.

20. A method of claim 18 further including the steps of providing a binder wherein the fibrillated nanofibers and binder are wet laid or coated from a fluid suspension onto the existing filter medium.

* * * * *